(12) United States Patent
Subbarao et al.

(10) Patent No.: US 11,389,133 B2
(45) Date of Patent: Jul. 19, 2022

(54) METHOD AND APPARATUS FOR FOLLICULAR QUANTIFICATION IN 3D ULTRASOUND IMAGES

(71) Applicant: SAMSUNG ELECTRONICS CO., LTD., Suwon-si (KR)

(72) Inventors: Nikhil Narayan Subbarao, Bangalore (IN); Srinivasan Sivanandan, Chennai (IN); Kedar Anil Patwardhan, Pune (IN); Srinivas Rao Kudavelly, Bangalore (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 368 days.

(21) Appl. No.: 16/345,056

(22) PCT Filed: Oct. 23, 2017

(86) PCT No.: PCT/KR2017/011719
§ 371 (c)(1),
(2) Date: Apr. 25, 2019

(87) PCT Pub. No.: WO2018/080120
PCT Pub. Date: May 3, 2018

(65) Prior Publication Data
US 2019/0307417 A1  Oct. 10, 2019

(30) Foreign Application Priority Data

Oct. 28, 2016 (IN) .............................. 201641037102
Jul. 24, 2017 (IN) .............................. 201641037102

(51) Int. Cl.
*A61B 8/08* (2006.01)
*A61B 8/00* (2006.01)
(Continued)

(52) U.S. Cl.
CPC ................ *A61B 8/085* (2013.01); *A61B 8/08* (2013.01); *A61B 8/463* (2013.01); *A61B 8/483* (2013.01);
(Continued)

(58) Field of Classification Search
CPC ......... A61B 8/085; A61B 8/5223; A61B 8/08; A61B 8/463; A61B 8/483; A61B 8/0841;
(Continued)

(56) References Cited

U.S. PATENT DOCUMENTS

2004/0224895 A1  11/2004 Franks et al.
2014/0031691 A1   1/2014 Nagase et al.
(Continued)

FOREIGN PATENT DOCUMENTS

KR   10-2011-0080517 A    7/2011
WO      2015/158875 A1   10/2015

OTHER PUBLICATIONS

Baerwald AR, Walker RA, Pierson RA. Growth rates of ovarian follicles during natural menstrual cycles, oral contraception cycles, and ovarian stimulation cycles. Fertil Steril. Feb. 2009;91(2):440-9. Epub Feb. 4, 2008. (Year: 2009).*

(Continued)

*Primary Examiner* — Amelie R Davis
*Assistant Examiner* — Helene Bor
(74) *Attorney, Agent, or Firm* — Sughrue Mion, PLLC

(57) ABSTRACT

Provided are a method and a ultrasound imaging apparatus for managing growth of follicles in an ovary where the method comprises detecting, by a signal processor, the follicles and a plurality of parameters associated with each follicle in a three dimensional (3D) ultra sound image, tracking the detected follicles in a longitudinal scan, monitoring a rate of growth of each follicle based on the detected parameters in the longitudinal scan, determining a dosage of (Continued)

hormone for stimulating the ovary based on the rate of growth of each follicle, and generating a report and a nomograph based on the rate of growth of each follicle.

13 Claims, 13 Drawing Sheets

(51) Int. Cl.
 *G06K 9/62* (2022.01)
 *A61B 8/12* (2006.01)
(52) U.S. Cl.
 CPC .......... *A61B 8/5223* (2013.01); *G06K 9/6224* (2013.01); *A61B 8/0841* (2013.01); *A61B 8/12* (2013.01); *A61B 8/469* (2013.01)
(58) Field of Classification Search
 CPC ........ A61B 8/12; A61B 8/469; G06K 9/6224; G16H 50/30
 See application file for complete search history.

(56) References Cited

U.S. PATENT DOCUMENTS

| | | | | |
|---|---|---|---|---|
| 2016/0030011 | A1* | 2/2016 | James | A61B 5/7275 600/549 |
| 2016/0063695 | A1* | 3/2016 | Lee | G06K 9/6201 382/131 |
| 2016/0186262 | A1* | 6/2016 | Johnson | C12Q 1/6869 506/2 |
| 2016/0292848 | A1* | 10/2016 | Plakas | A61B 8/085 |
| 2018/0144470 | A1* | 5/2018 | Govindjee | A61B 5/7275 |

OTHER PUBLICATIONS

Salama S, Arbo E, Lamazou F, Levailllant JM, Frydman R, Fanchin R. Reproducibility and reliability of automated volumetric measurement of single preovulatory follicles using SonoAVC. Fertil Steril. Apr. 2010;93(6):2069-73. Epub Apr. 1, 2009. (Year: 2010).*
Deutsch, Todd D, and Alfred Z Abuhamad. Sonography-Based Automated Volume Count (SonoAVC): an Efficient and Reproducible Method of Follicular Assessment. General Electric Company, 2007, www.volusonclub.net/data/pages/assisted-reproductive-technology/Sonography-based_Automated_Volume_Count.pdf. (Year: 2007).*
Sarty GE, Pierson RA. An application of Lacker's mathematical model for the prediction of ovarian response to superstimulation. Math Biosci. Nov. 2005;198(1):80-96. Epub Sep. 26, 2005. (Year: 2005).*
Cedrin-Durnerin I, Massin N, Galey-Fontaine J, Bry-Gauillard H, Roger M, Lahlou N, Hugues JN. Timing of FSH administration for ovarian stimulation in normo-ovulatory women: comparison of an early or a mid follicular phase initiation of a short-term treatment. Hum Reprod. Nov. 2006;21(11):2941-7 (Year: 2006).*
Nyboe Andersen A, Balen A, Platteau P, Devroey P, Helmgaard L, Arce JC; Bravelle Ovulation Induction (BOI) Study Group. Predicting the FSH threshold dose in women with WHO Group II anovulatory infertility failing to ovulate or conceive on clomiphene citrate. Hum Reprod. Jun. 2008;23(6):1424-30. (Year: 2008).*
T. Chen, Wei Zhang, S. Good, K. S. Zhou and D. Comaniciu, "Automatic ovarian follicle quantification from 3D ultrasound data using global/local context with database guided segmentation," 2009 IEEE 12th International Conference on Computer Vision, Kyoto, Japan, 2009, pp. 795-802 (Year: 2009).*
NIC Freiesleben et al. "Predictors of ovarian response in intrauterine insemination patients and development of a dosage nomogram". Reproductive BioMedicine Online. vol. 17, No. 5 (2008) p. 632-641 (Year: 2008).*
International Search Report and Written Opinion dated Feb. 8, 2018 issued by the International Searching Authority in counterpart International Application No. PCT/KR2017/011719 (PCT/ISA/220, PCT/ISA/210, PCT/ISA/237).
Comaniciu et al., "Mean Shift: A Robust Approach Toward Feature Space Analysis", IEEE Transactions on Pattern Analysis and Machine Intelligence, vol. 24, No. 5, May 2002, pp. 603-619, 17 pages total.
Kovesi, "Symmetry and Asymmetry from Local Phase", Tenth Australian Joint Conference on Artificial Intelligence, vol. 190, 1997, 6 pages total.
"Ultrasound Imaging in Reproductive Medicine : Advances in Infertility Work-up, Treatment & ART", Abstract and References, 2013, 30 pages total, https://link.springer.com/chapter/10.1007/978-1-4614-9182-8_20, first online Nov. 12, 2013, copyright 2014.
Chen et al., "Automatic ovarian follicle quantification from 3D ultrasound data using global/local context with database guided segmentation", IEEE 12th International Conference, 2009, 8 pages total.
"5D Follicle module on the Samsung WS80A imaging workstation", 24 pages total, https://www.samsunghealthcare.com/en/products/UltrasoundSystem/WS80A%20with%20Elite/Obstetrics%20-%20Gynecology/benefit, copyright 2016-2018.

\* cited by examiner

[Figure 1]
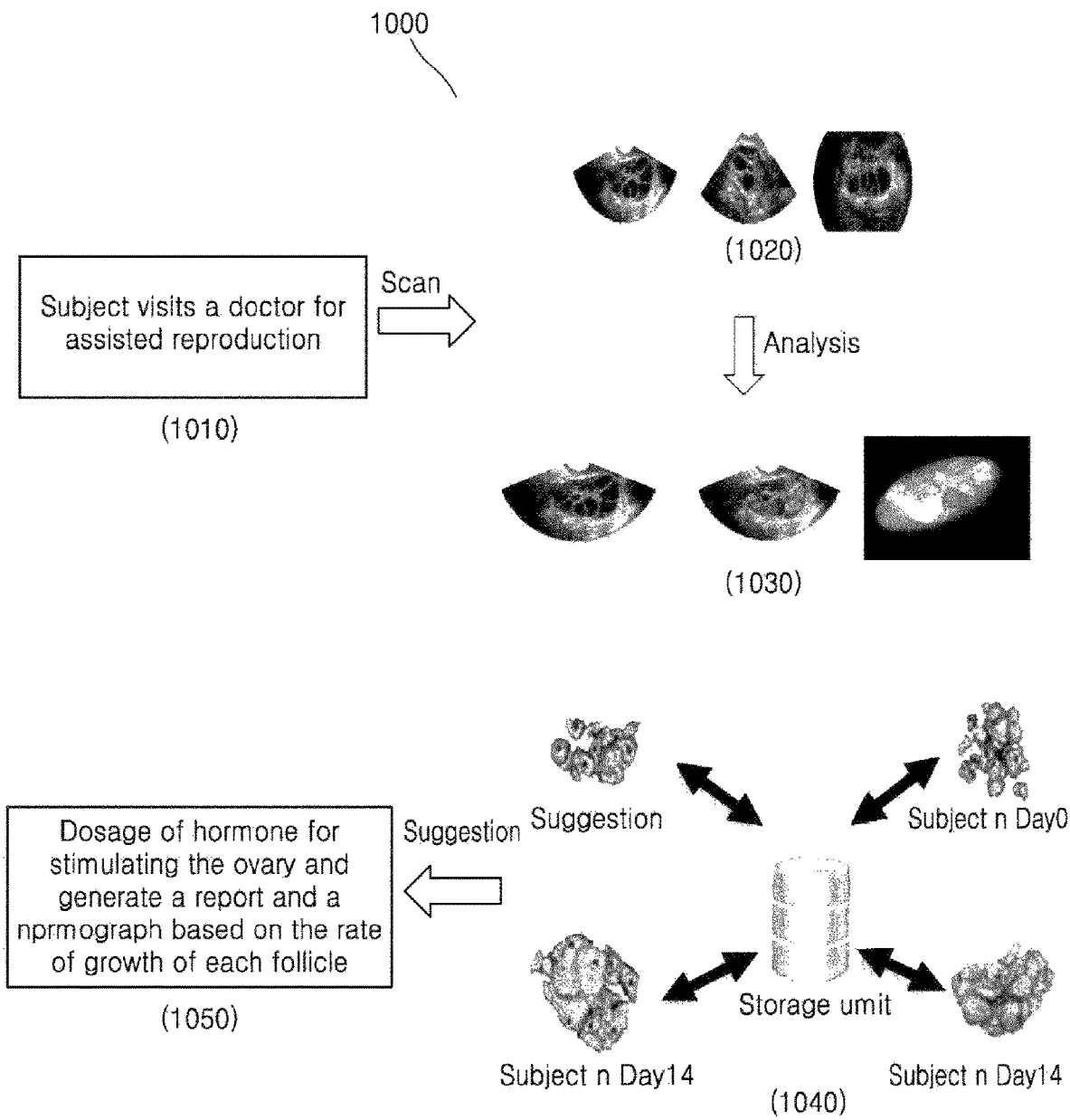

[Figure 2A]
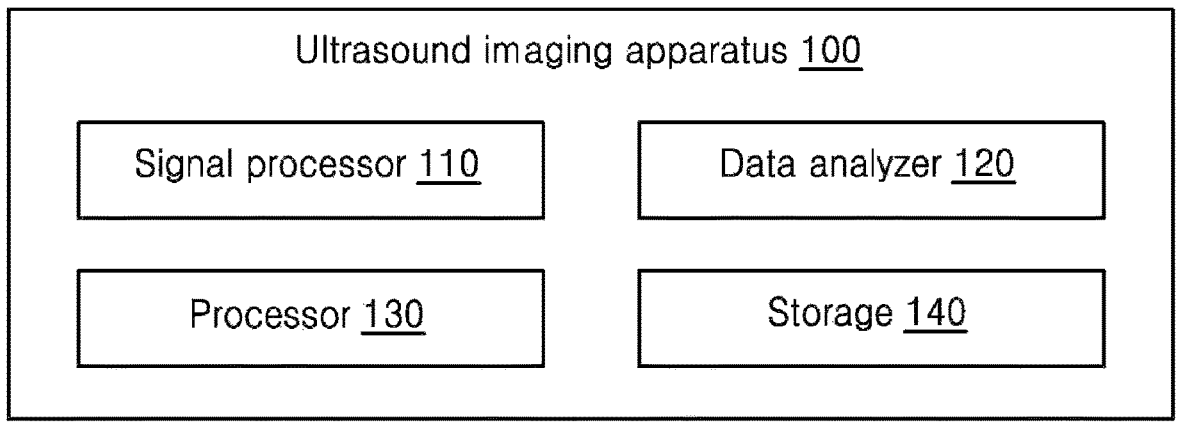
[Figure 2B]
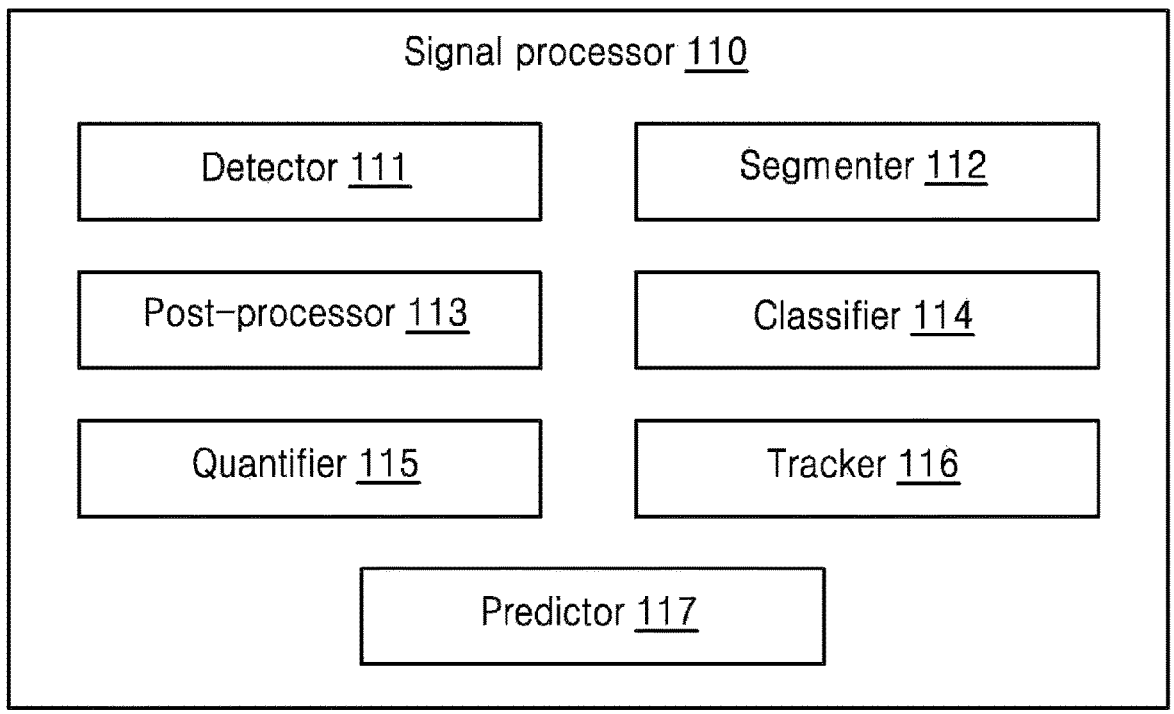

[Figure 3]
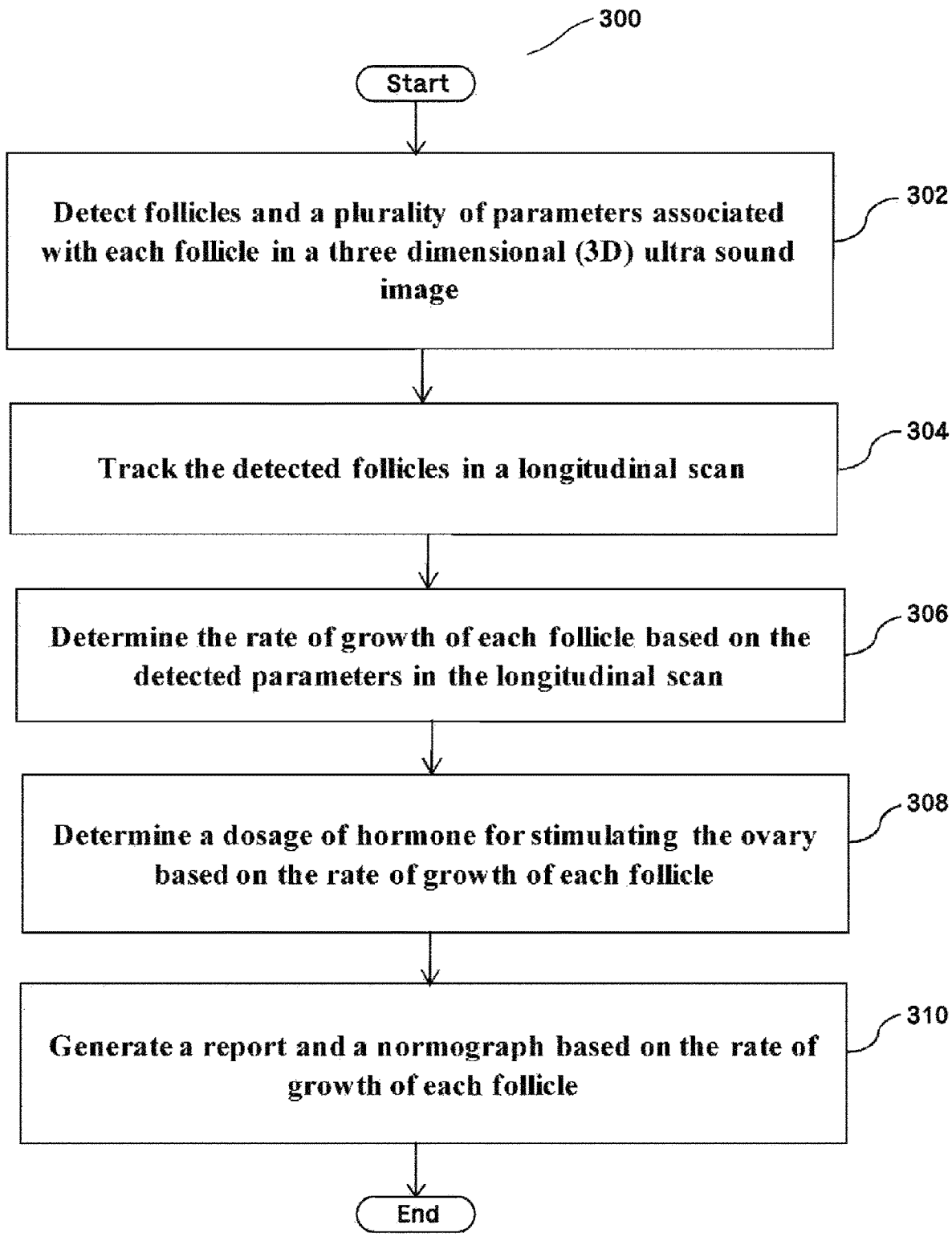

[Figure 4]
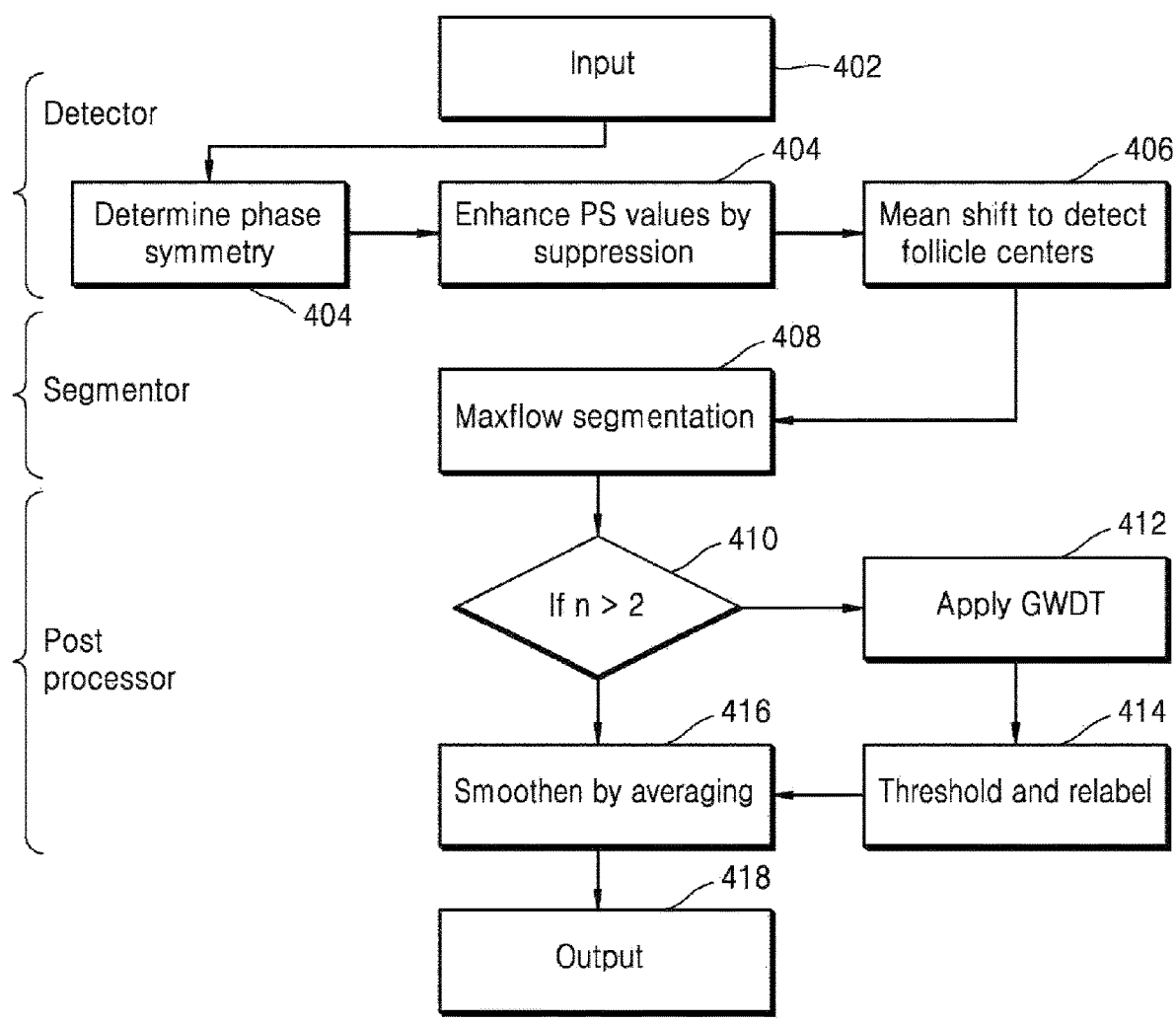

【Figure 5】
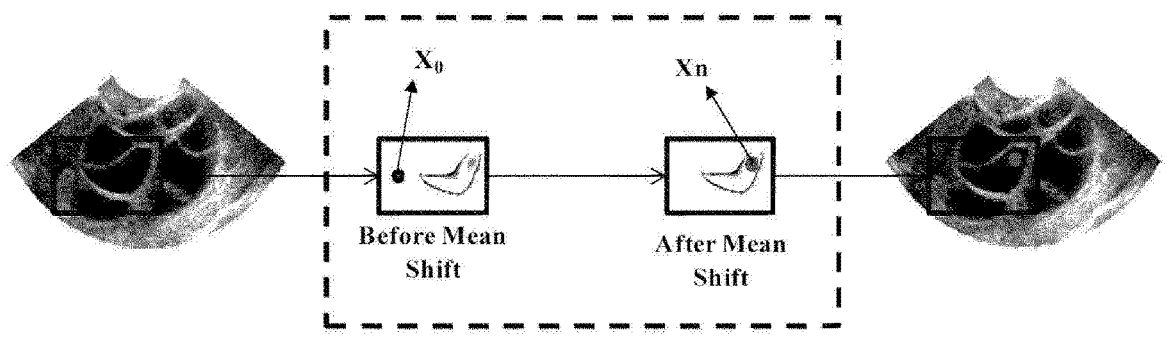
【Figure 6】
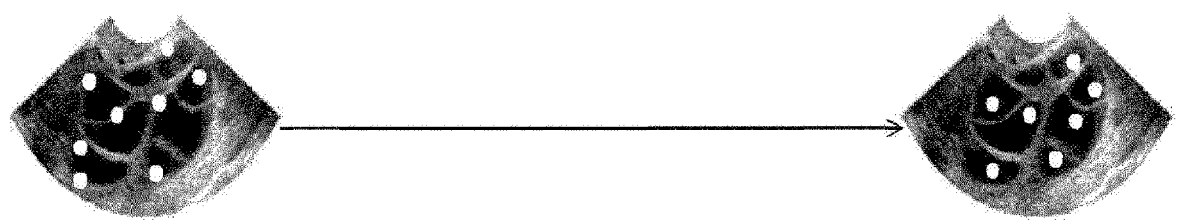

[Figure 7]
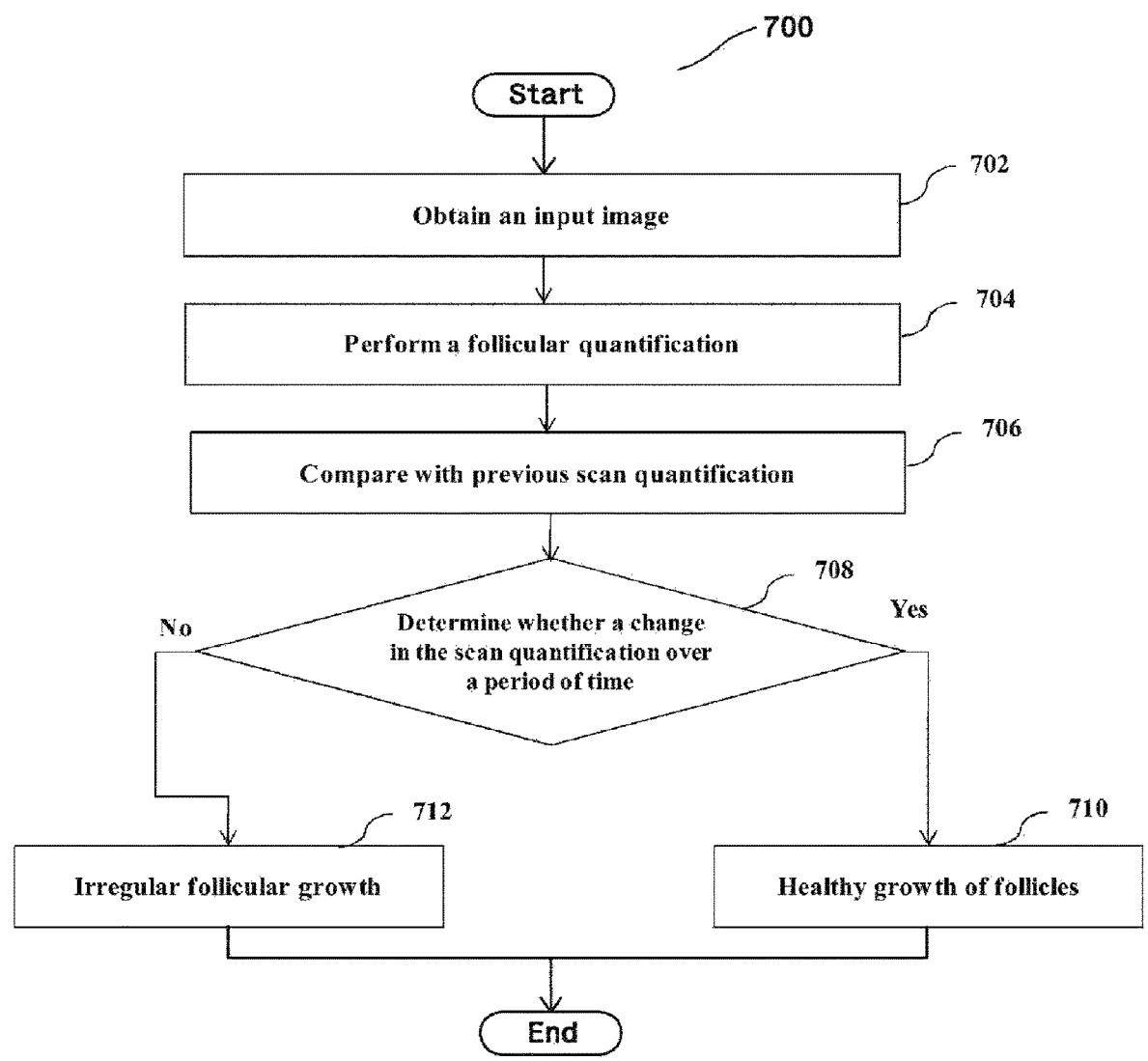

[Figure 8]
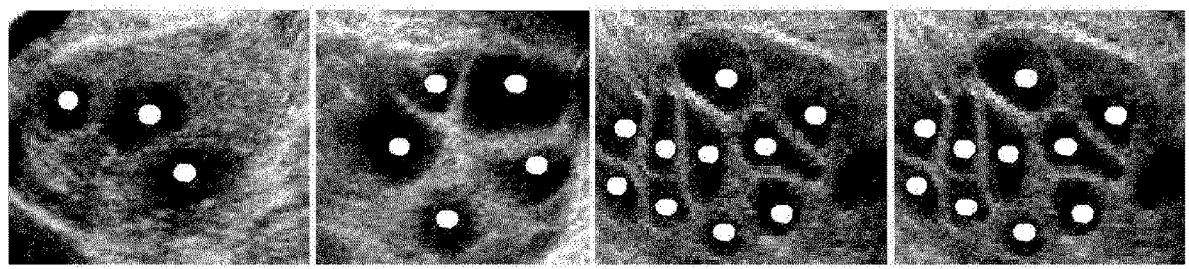
Day 2;
Follicles = 3
Day 3;
Follicles = 5
Day 4;
Follicles = 10
Day 5;
Follicles = 10

[Figure 9]
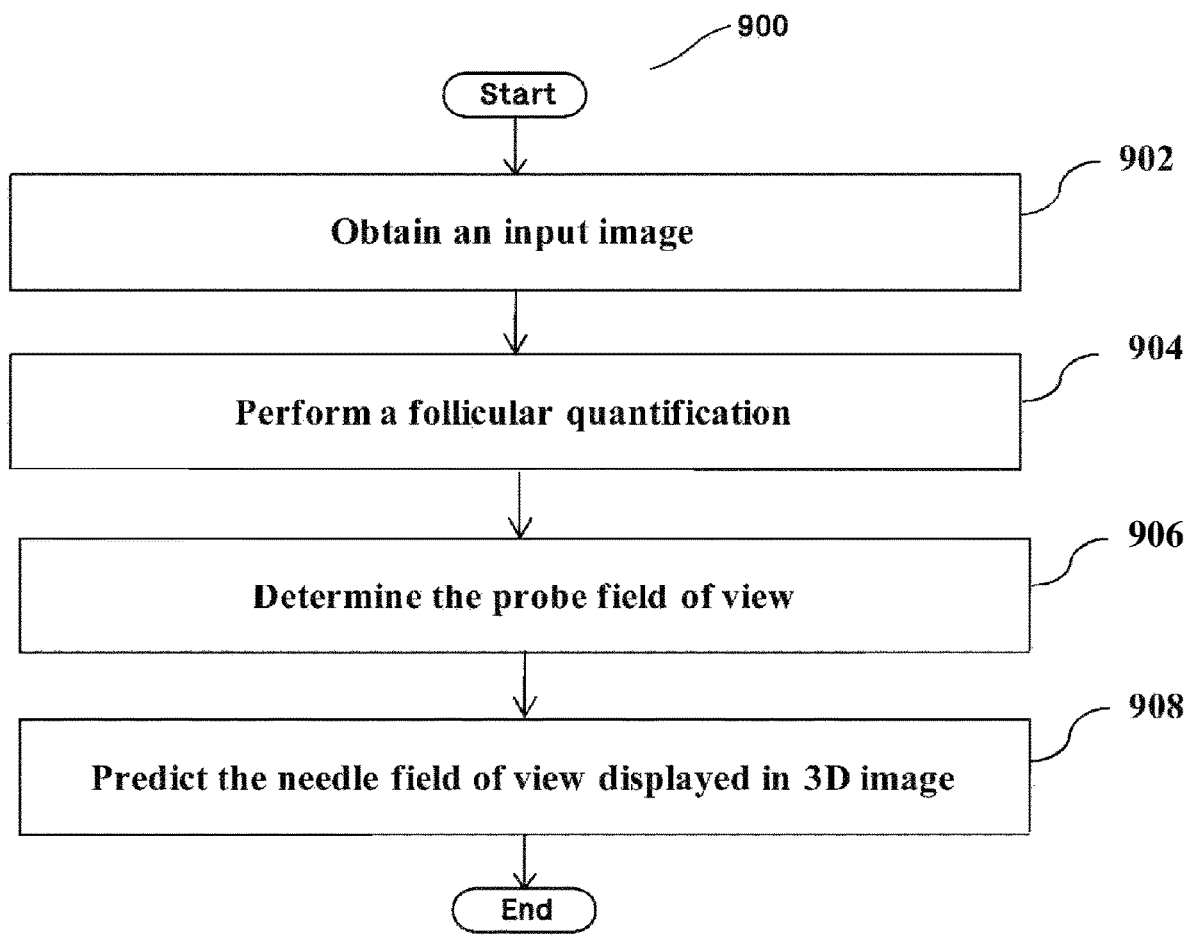

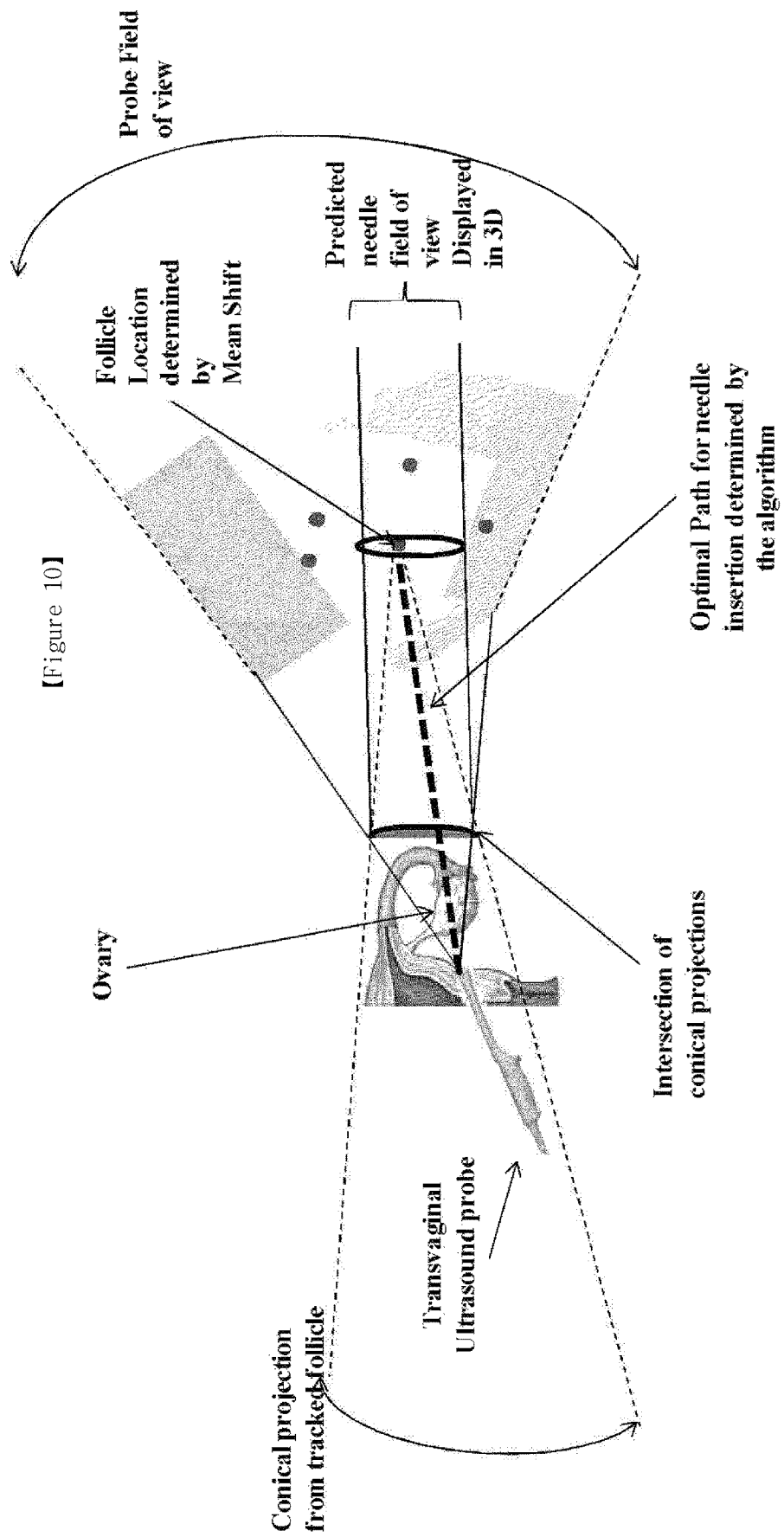
[Figure 10]

[Figure 11]
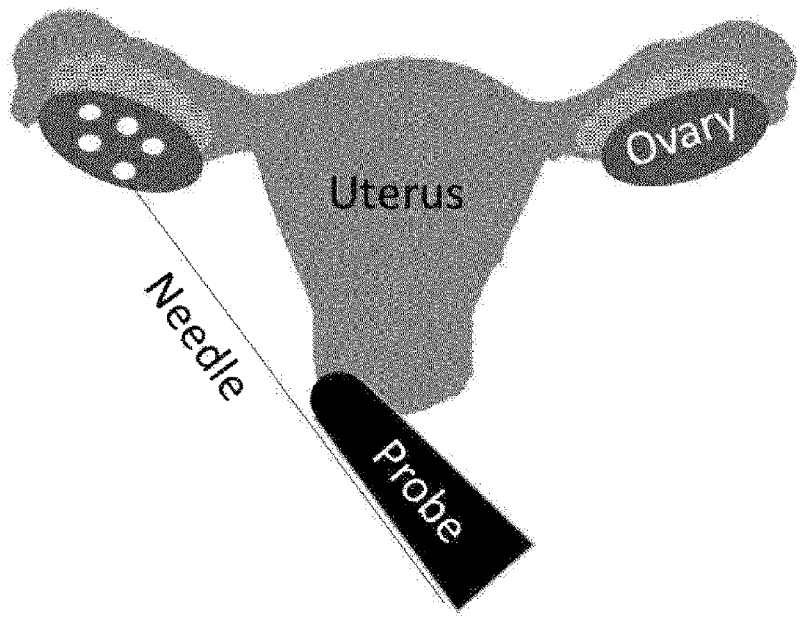
[Figure 12]
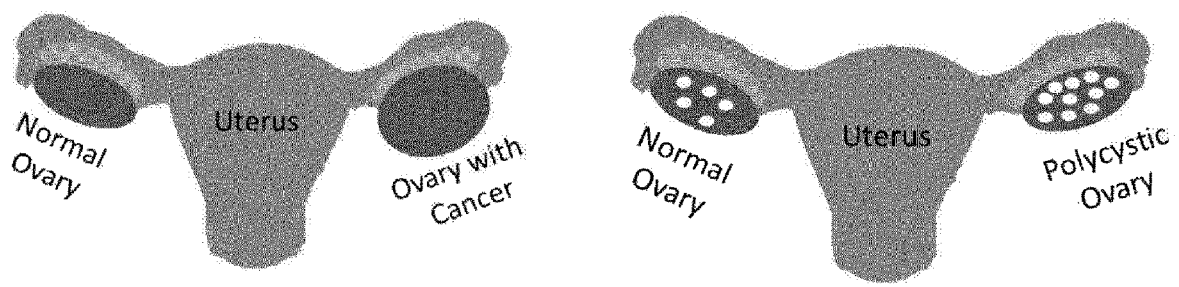

[Figure 13]
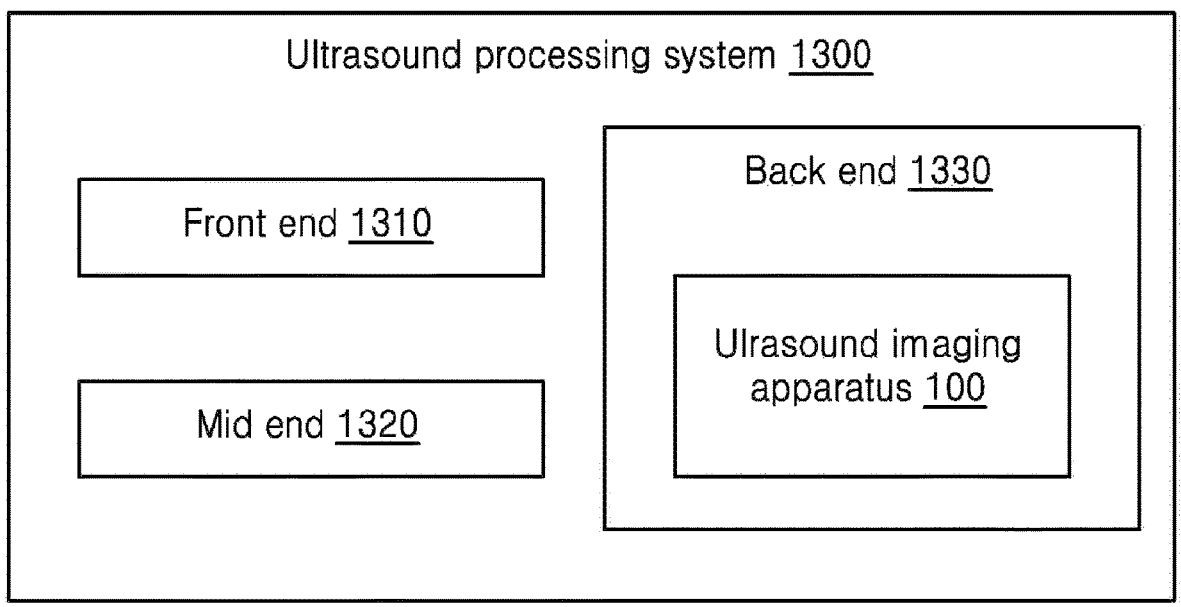

【Figure 14】
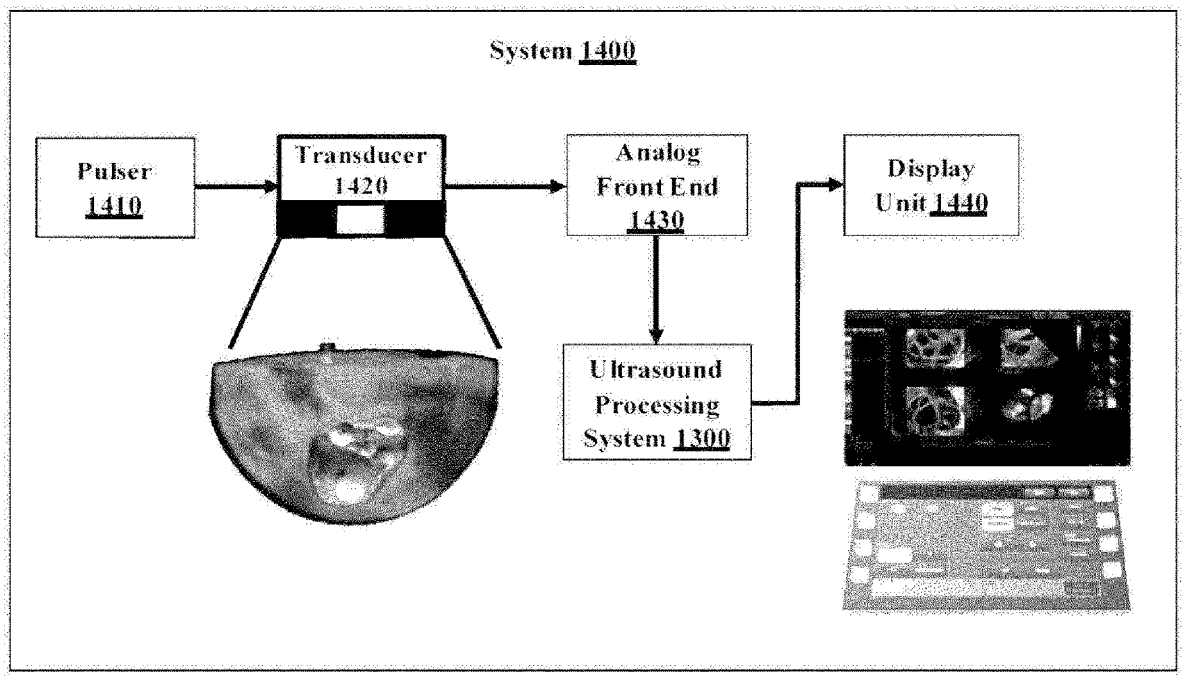

[Figure 15]
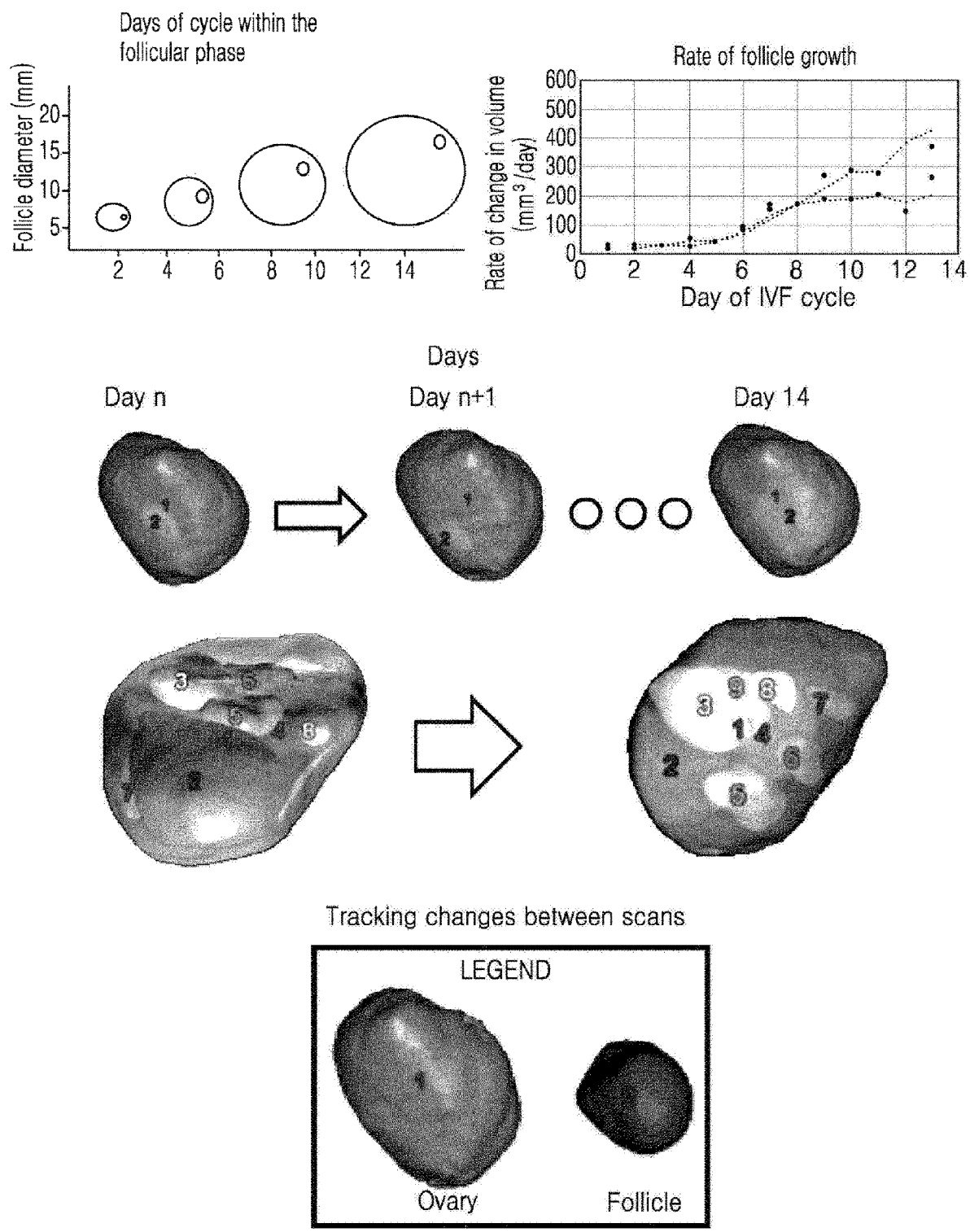

METHOD AND APPARATUS FOR FOLLICULAR QUANTIFICATION IN 3D ULTRASOUND IMAGES

TECHNICAL FIELD

The present disclosure relates to a medical system, and more particularly to a method and ultrasound imaging apparatus for managing growth of follicles in an ovary.

BACKGROUND ART

Follicles are anatomical structures for the development of ova in ovaries of a human female reproductive system. About 9-12 follicles are synthesized in an ovary in a single menstrual cycle. Only one dominant follicle grows enough to generate an ovum that is released in the middle of a monthly cycle. In abnormal ovaries, the dominant follicle that accommodates the ovum does not grow fully or has arrested growth. Under such circumstances, assisted reproduction is employed where a mature egg is extracted from the follicle to perform in-vitro fertilization (IVF) and the fertilized egg is embedded in the wall of the uterus. Selection of the mature egg requires identification of the dominant follicle. The dominant follicle can be determined by hyperstimulating the ovary by injecting hormones necessary for follicular growth. The dosage of the hormones to be administered depends on the number of follicles, the sizes of the follicles, and the rate of previous growth of the follicles in the ovary.

Further, the rate of growth of follicles in the ovary is determined by using an ultrasound imaging apparatus. The ultrasound imaging apparatus irradiates an ultrasound signal, generated by a transducer of a probe, to the ovary and receives information via an echo signal reflected from the ovary, thereby obtaining an image of internal portions of the ovary. In particular, the ultrasound imaging apparatus is used for medical purposes, such as observation of the inside of the ovary, and diagnosis of damage to an internal portion of the ovary.

However, the existing methods do not track the growth of follicles at regular time intervals, so there is a need for a robust method and system for automatic follicle quantification and tracking of follicle growth.

Thus, it is desired to address the above mentioned disadvantages and other shortcomings or at least provide a useful alternative.

DISCLOSURE

Technical Solution

Accordingly, provided is a method of managing growth of follicles in an ovary. The method includes detecting, by a signal processor, the follicles and a plurality of parameters associated with each follicle in a 3D ultra sound image. Further, the method includes tracking, by the signal processor, the detected follicles in a longitudinal scan. Further, the method includes monitoring, by the signal processor, a rate of growth of each follicle based on the detected parameters in the longitudinal scan. Further, the method includes determining, by the signal processor, a dosage of hormone for stimulating the ovary based on the rate of growth of each follicle. Further, the method includes generating, by a data analyzer, a report and a nomograph based on the rate of growth of each follicle.

Advantageous Effects

The present methods track the growth of follicles at regular time intervals, so provided are a robust method and system for automatic follicle quantification and tracking of follicle growth.

DESCRIPTION OF DRAWINGS

Reference will now be made in greater detail to various example embodiments, examples of which are illustrated in the accompanying drawings, wherein like reference numbers refer to like elements in the various figures. The example embodiments herein will be better understood from the following description with reference to the drawings, in which:

FIG. 1 is a schematic diagram showing an example scenario in which an ultrasound imaging apparatus is configured to manage the growth of follicles in an ovary, according to an exemplary embodiment;

FIG. 2A is a block diagram of the ultrasound imaging apparatus, including various hardware elements, for managing the growth of the follicles in the ovary, according to an exemplary embodiment;

FIG. 2B is a block diagram of a signal processor, including various hardware elements, for managing growth of the follicles in the ovary, according to an exemplary embodiment;

FIG. 3 is a flowchart of a method of managing the growth of the follicles in the ovary, according to an exemplary embodiment;

FIG. 4 is a flowchart illustrating sequential step by step procedures for follicular quantification in an ultrasound image of the ovary, according to an exemplary embodiment;

FIG. 5 is a schematic diagram showing an example scenario in which a single follicle is detected based on a mean shift procedure, according to an exemplary embodiment;

FIG. 6 is a schematic diagram showing an example scenario in which multiple follicles are detected based on the mean shift procedure, according to an exemplary embodiment;

FIG. 7 is a flowchart of a method of monitoring a growing condition of follicles in the ovary, according to an exemplary embodiment;

FIG. 8 is a diagram showing an example scenario in which a growing condition of follicles is determined based on a change in a scan quantification over a period of time, according to an exemplary embodiment;

FIG. 9 is a flowchart exemplarily illustrating a method of needle path tracking for egg retrieval from a dominant follicle, according to an exemplary embodiment;

FIG. 10 is an example scenario in which needle path tracking for egg retrieval from dominant follicle is depicted, according to an exemplary embodiment;

FIG. 11 is an example scenario in which spatial locations of the follicles is used for surgical planning and needle insert ion for the egg retrieval, according to an exemplary embodiment;

FIG. 12 is a schematic diagram showing an example scenario in which a number and echogenicity of the follicle and an echogenicity of the ovary are used for computer aided diagnosis (CAD), according to an exemplary embodiment;

FIG. 13 is a schematic diagram of a system for processing the ultrasound image, according to an exemplary embodiment;

FIG. 14 is a schematic diagram of a system for acquiring and processing the ultrasound image, according to an exemplary embodiment; and FIG. 15 is a schematic diagram including a nomograph illustrating the rate of growth of each follicle, according to an exemplary embodiment.

BEST MODE

Accordingly, exemplary embodiments disclosed herein provide a method of managing growth of follicles in an ovary. The method includes detecting, by a signal processor, the follicles and a plurality of parameters associated with each follicle in a 3D ultra sound image. Further, the method includes tracking, by the signal processor, the detected follicles in a longitudinal scan. Further, the method includes monitoring, by the signal processor, a rate of growth of each follicle based on the detected parameters in the longitudinal scan. Further, the method includes determining, by the signal processor, a dosage of hormone for stimulating the ovary based on the rate of growth of each follicle. Further, the method includes generating, by a data analyzer, a report and a nomograph based on the rate of growth of each follicle.

In an exemplary embodiment, the plurality of parameters includes at least one of the number of follicles in the ovary, size of the follicle, volume of the follicle in the ovary, diameter of the follicle, an average length of the follicle, an identity of the follicle, and a location of the follicle in the ovary with respect to a plurality of an anatomical landmark.

In an exemplary embodiment, the plurality of anatomical landmarks includes at least one of ovarian vessels, an endometrium, a boundary of an uterus, fallopian tubes, medulla of the ovary, a soft tissue in the ovary, the junctional zone, a corpus luteum, imaging artifacts and anatomical structures that are visible in the ultrasound image.

In an exemplary embodiment, the follicles is detected by detecting at least one portion of the follicles by a mean-shift clustering procedure on a local phase likelihood map, segmenting the follicles by a graph based procedure, and post-processing the segmented follicles using statistical, morphological and distance based methods.

In an exemplary embodiment, the longitudinal scan includes a set of images obtained at different time intervals.

In an exemplary embodiment, the detected follicles is tracked by correlating the identity of the detected follicle at the current time with its identity in the longitudinal scan based on the location of the follicle in the ovary with respect to a plurality of anatomical landmarks.

In an exemplary embodiment, the rate of growth of each follicle is monitored by obtaining the parameters associated with each follicle in the longitudinal scans, storing the obtained parameters, and determining the rate of growth of each follicle based on comparison of the parameters.

In an exemplary embodiment, the method further includes predicting the growth of each follicle based on the stored parameters. Further, the method includes calculating difference between predicted growth of each follicle and the determined growth of each follicle periodically. Further, the method includes dynamically determining the dosage of the hormone based on the calculated difference.

In an exemplary embodiment, the report and the nomograph are generated by plotting a growth rate of the follicles over time, plotting the dosage administered over time, predicting the ovarian response, categorizing a subject into a first(poor) responder and a second(good) responder based on the ovarian response, and generating a document consolidating and/or merging the plurality of parameters with regard to detecting, tracking and monitoring of follicle growth along with the predicted and actual dosage and predicted outcomes.

In an exemplary embodiment, the parameters associated with each follicle are continuously monitored for diagnosing disorders in the ovary.

Accordingly, exemplary embodiments herein disclose an ultrasound imaging apparatus for managing growth of follicles in an ovary. The ultrasound imaging apparatus comprises a signal processor coupled with a processor and ultrasound imaging a storage. The signal processor is configured to detect the follicles and a plurality of parameters associated with each follicle in a 3D ultra sound image. Further, the signal processor is configured to track the detected follicles in a longitudinal scan. Further, the signal processor is configured to monitor a rate of growth of each follicle based on the detected parameters in the longitudinal scan. Further, the signal processor is configured to determine a dosage of hormone for stimulating the ovary based on the rate of growth of each follicle. Further, the signal processor is configured to generate a report and a nomograph based on the rate of growth of each follicle.

These and other aspects of the exemplary embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

Mode for Invention

Exemplary embodiments herein and various features and advantageous details thereof will now be explained more fully with reference to non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those of ordinary skill in the art to practice the embodiments. Accordingly, the examples should not be construed as limiting the scope of the embodiments herein.

As is traditional in the field, embodiments may be described and illustrated in terms of blocks which carry out a described function or functions. These blocks, which may be referred to herein as units or modules or the like, may be physically implemented by analog or digital circuits such as logic gates, integrated circuits, microprocessors, microcontrollers, memory circuits, passive electronic components, active electronic components, optical components, hardwired circuits, or the like, and may optionally be driven by firmware and software. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the invention. Likewise, the blocks of the embodiments may be physically combined into more complex blocks without departing from the scope of the invention The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings. Although the terms first, second, etc. may be used herein to describe various elements, these elements should not be limited by these terms. These terms are generally only used to distinguish one element from another.

The exemplary embodiments herein provide a method of managing growth of follicles in an ovary. The method includes detecting, by a signal processor, the follicles and a plurality of parameters associated with each follicle in a 3D ultra sound image. Further, the method includes tracking, by the signal processor, the detected follicles in a longitudinal scan. Further, the method includes monitoring, by the signal processor, a rate of growth of each follicle based on the detected parameters in the longitudinal scan. Further, the method includes determining, by the signal processor, a dosage of hormone for stimulating the ovary based on the rate of growth of each follicle. Further, the method includes generating, by a data analyzer, a report and a nomograph based on the rate of growth of each follicle.

Unlike conventional methods and systems, the proposed method can be used to provide an accurate quantification of the follicles in the ovary at regular time intervals by tracking detected follicles during the longitudinal scan.

The method can be used to automatically perform the follicle quantification (e.g., determining the size of follicles, number of follicles, location of follicles, or the like) in the 3D ultrasound images for longitudinal tracking of the follicles and ovarian quantification to create a subject specific model (e.g., patient specific model) for hormone dosage prediction in assisted reproduction in an effective and accurate manner.

The proposed method can be used to automatically perform ovarian quantification. The proposed method can be used to obtain an automatic region of interest (ROI) for follicle quantification.

The proposed method can be used to enable longitudinal tracking of the follicles with high detection rates and accurate spatial localization. The proposed method can be used to predict the rate of growth of the dominant follicle from a previous cycle. The proposed method can be used to provide automatic dosage quantification and achieve a high sensitivity and accurate spatial localization using a mean shift procedure in conjunction with a phase symmetry procedure.

Exemplary embodiments will now be described below by referring to the drawings of FIGS. 1 through 15.

FIG. 1 is a schematic diagram showing an example scenario 1000 in which an ultrasound imaging apparatus 100 (not shown) is configured to manage the growth of follicles in an ovary, according to an exemplary embodiment. In the scenario, a subject (e.g., a patient, or the like) visits a doctor (e.g., a gynecologist) for assisted reproduction in 1010 of FIG. 1. Further, the doctor scans the ovary of the subject based on a 3D ultrasound imaging in 1020 of FIG. 1.

Based on the scan, the ultrasound imaging apparatus 100 is configured to receive a scan image (e.g. a 3D ultrasound image) corresponding to the ovary of the subject. After receiving the scan image, the ultrasound imaging apparatus 100 is configured to detect the follicles and a plurality of parameters associated with each follicle in the 3D ultrasound image.

In an exemplary embodiment, the plurality of parameters includes at least one of a number of follicles in the ovary, a size of the follicle, a volume of the follicle in the ovary, a diameter of the follicle, an average length of the follicle, an identity of the follicle, and a location of the follicle in the ovary with respect to a plurality of an anatomical landmark.

In an exemplary embodiment, the plurality of anatomical landmarks includes of at least one of ovarian vessels, an endometrium, a boundary of the uterus, fallopian tubes, medulla of the ovary, a soft tissue in the ovary, the junctional zone, a corpus luteum, imaging artifacts and anatomical structures that are visible in the 3D ultrasound image.

In an exemplary embodiment, the follicles are detected by detecting at least one portion of the follicles by a mean-shift clustering procedure on a local phase likelihood map, segmenting the follicles by a graph based procedure, and post-processing the segmented follicles using statistical, morphological and distance based procedures.

Based on the detected follicles and the plurality of parameters associated with each follicle in the 3D ultrasound image, the ultrasound imaging apparatus 100 is configured to track the detected follicles in a longitudinal scan. In an exemplary embodiment, the longitudinal scan includes a set of images obtained at different time intervals.

In an exemplary embodiment, the detected follicles is tracked by correlating the identity of the detected follicle at the current time with its identity in the longitudinal scans based on the location of the follicle in the ovary with respect to a plurality of anatomical landmarks.

Further, the ultrasound imaging apparatus 100 is configured to monitor a rate of growth of each follicle based on the detected parameters in the longitudinal scan. In an exemplary embodiment, the rate of growth of each follicle is monitored by obtaining the parameters associated with each follicle in the longitudinal scans, storing the obtained parameters, and determining the rate of growth of each follicle based on comparison of the parameters in 1040 of FIG. 1.

Based on the rate of growth of each follicle, the ultrasound imaging apparatus 100 is configured to determine the dosage of hormone for stimulating the ovary. Further, the ultrasound imaging apparatus 100 is configured to generate a report and a nomograph based on the rate of growth of each follicle in 1050 of FIG. 1.

In an exemplary embodiment, the ultrasound imaging apparatus 100 is configured to predict the growth of each follicle based on the stored parameters. Further, the ultrasound imaging apparatus 100 is configured to calculate difference between predicted growth of each follicle and the determined growth of each follicle periodically. Further, the ultrasound imaging apparatus 100 is configured to dynamically determine the dosage of the hormone based on the calculated difference.

In an exemplary embodiment, the report and the nomograph are generated by plotting a growth rate of the follicles over time, plotting the dosage administered over time, predicting the ovarian response, categorizing the subject into a first(poor) responder and a second(good) responder based on the ovarian response, and generating a document consolidating and/or merging the plurality of parameters with regard to detecting, tracking and monitoring of follicle growth along with the predicted and actual dosage and predicted outcomes.

In an exemplary embodiment, the parameters associated with each follicle are continuously monitored for diagnosing disorders in the ovary.

In an exemplary embodiment, the ultrasound imaging apparatus 100 is configured to determine the rate of follicular growth and the dosage of hormones to be administered based on the spatial locations of the follicles at the time instant and the administered dosage of hormones for the subject at the time instant.

In an exemplary embodiment, the ultrasound imaging apparatus 100 is configured to perform the follicle and ovary quantification and load previous quantification results of the subject from a storage (not shown). Further, the ultrasound imaging apparatus 100 is configured to track the follicular growth and predict the hormone dosage to be administered and store the information (e.g., hormone dosage) in the storage.

In the proposed systems, the predicted hormone drug dosage is used to maintain an inventory of drugs needed for reproductive medicine. The longitudinal tracked follicles saved in the storage (e.g., cloud based storage, or the like) assists in devising patient specific models for procedures in the reproductive medicine. The spatial locations of the tracked follicles is used for surgical planning and needle insertion for an egg retrieval procedure. The number and echogenicity of the tracked follicle and the echogenicity of the ovary is used for a Computer Aided Diagnosis (CAD) e.g., Polycystic Ovary Syndrome (PCOS), ovarian cancer, or the like.

In an exemplary embodiment, the 3D ultrasound images are used for follicle quantification, tracking follicles' growth rate, administering dosage, and predicting hormone dosage or the like.

In an exemplary embodiment, the ultrasound imaging apparatus 100 is configured to receive the input 3D ultrasound image corresponding to the ovary of the subject. Further, the ultrasound imaging apparatus 100 is configured to determine the number of follicles in the ovary. Further, the ultrasound imaging apparatus 100 is configured to compute the size of the follicles in the ovary. Further, the ultrasound imaging apparatus 100 is configured to determine the ovarian volume. Further, the ultrasound imaging apparatus 100 is configured to determine the spatial locations of the follicles within the ovary. Further, the ultrasound imaging apparatus 100 is configured to load previously computed spatial locations of the subject under consideration from the storage. Further, the ultrasound imaging apparatus 100 is configured to load the previously administered dosage of hormones for the specific subject from the storage. Further, the ultrasound imaging apparatus 100 is configured to determine the rate of follicular growth. Further, the ultrasound imaging apparatus 100 is configured to determine the dosage of hormones to be administered. Further, the ultrasound imaging apparatus 100 is configured to predict the rate of follicular growth. Further, the ultrasound imaging apparatus 100 is configured to predict the dosage for the next sitting of the subject under consideration.

FIG. 1 gives a limited overview of the ultrasound imaging apparatus 100 but, it is to be understood that other embodiments are not limited thereto. Further, the ultrasound imaging apparatus 100 includes any number of hardware or software components communicating with each other. By way of illustration, both an application running on a device and the device itself can be a component.

FIG. 2A is a block diagram of the ultrasound imaging apparatus 100, including various hardware elements, for managing growth of the follicles in the ovary, according to an exemplary embodiment. In an exemplary embodiment, the ultrasound imaging apparatus 100 includes a signal processor 110, a data analyzer 120, a processor 130, and a storage 140. According to a designer's choice, the signal processor 110, a data analyzer 120, and a processor 130 can be implemented as a single(signal) processor. The processor 130 is in communication with the signal processor 110, the data analyzer 120, and the storage 140. The signal processor 110 is configured to receive the scan image (e.g. 3D ultrasound image) corresponding to the ovary of the subject. After receiving the scan image, the signal processor 110 is configured to detect the follicles and the plurality of parameters associated with each follicle in the 3D ultrasound image.

In an exemplary embodiment, the follicles are detected by the mean-shift clustering procedure on the local phase likelihood map, segmenting the follicles by the graph based procedure, and post-processing the segmented follicles using the statistical, morphological and distance based procedure.

Based on the detected follicles and the plurality of parameters associated with each follicle in the 3D ultrasound image, the signal processor 110 is configured to track the detected follicles in the longitudinal scan. In an exemplary embodiment, the longitudinal scan includes the set of images obtained at different time intervals.

In an exemplary embodiment, the detected follicles is tracked by correlating the identity of the detected follicle at the current time with its identity in the longitudinal scans based on the location of the follicle in the ovary with respect to the plurality of anatomical landmarks.

Further, the signal processor 110 is configured to monitor the rate of growth of each follicle based on the detected parameters in the longitudinal scan. In an exemplary embodiment, the rate of growth of each follicle is monitored by obtaining the parameters associated with each follicle in the longitudinal scans, storing the obtained parameters, and determining the rate of growth of each follicle based on comparison of the stored parameters.

Based on the rate of growth of each follicle, the signal processor 110 is configured to determine the dosage of hormone for stimulating the ovary. Further, the data analyzer 120 is configured to generate the report and the nomograph based on the rate of growth of each follicle.

In an exemplary embodiment, the signal processor 110 is configured to predict the growth of each follicle based on the stored parameters. Further, the signal processor 110 is configured to calculate difference between predicted growth of each follicle and the determined growth of each follicle periodically. Further, the signal processor 110 is configured to dynamically determine the dosage of the hormone based on the calculated difference.

In an exemplary embodiment, the parameters associated with each follicle are continuously monitored for diagnosing disorders in the ovary.

In an exemplary embodiment, the signal processor 110 is configured to generate the rate of follicular growth and the dosage of hormones to be administered based on the spatial locations of the follicles at the time instant and the administered dosage of hormones for the subject at the time instant.

In an exemplary embodiment, the signal processor 110 is configured to perform the follicle and ovary quantification and load previous quantification results of the subject from the storage 140. Further, the signal processor 110 is configured to track the follicular growth and predict the hormone dosage to be administered and store the information (e.g., hormone dosage) in the storage 140.

The processor 130 is in communication with a communication unit (not shown). The communication unit is configured for communicating internally between internal units and with external devices via one or more networks. The storage 140 may include one or more computer-readable storage media. The storage 140 may include non-volatile storage elements. Examples of such non-volatile storage elements may include magnetic hard disc, optical discs, floppy discs, flash memories, or forms of electrically programmable memories (EPROM) or electrically erasable and programmable (EEPROM) memories. In addition, the storage 140 may, in some examples, be considered a non-transitory storage medium. The term "non-transitory" may indicate that the storage medium is not embodied in a carrier wave or a propagated signal. However, the term "non-transitory" should not be interpreted that the storage 140 is non-movable. In some examples, the storage can be configured to store larger amounts of information than a memory. In certain examples, a non-transitory storage medium may store data that can, over time, change (e.g., in Random Access Memory (RAM) or cache).

Although FIG. 2A shows the hardware components of the ultrasound imaging apparatus 100 but it is to be understood that other embodiments are not limited thereon. In other embodiments, the ultrasound imaging apparatus 100 may include less or more number of components. Further, the labels or names of the components are used only for illustrative purpose and does not limit the scope of the invention. One or more components can be combined together to perform same or substantially similar function to manage the growth of follicles in the ovary.

FIG. 2B is a block diagram of the signal processor 110, including various hardware elements, for managing growth of the follicles in the ovary, according to an exemplary embodiment. In an exemplary embodiment, the signal processor 110 includes a detector 111, a segmenter 112, a post-processor 113, a classifier 114, a quantifier 115, a tracker 116, and a predictor 117. The detector 111 can be, for example, but not limited to a global feature detector and a local feature detector. The segmenter 112 can be, for example, but not limited to a threshold based segmenter, a region based segmenter and a morphology based segmenter. The classifier 114 can be, for example, but not limited to a supervised classifier, an unsupervised classifier and a state space predictor. The post-processor 113 includes a spatial domain filter, a frequency domain filter and an order statistics filter.

In an exemplary embodiment, the detector 111 is configured to receive the scan image corresponding to the ovary of the subject. After receiving the scan image, the detector 111 is configured to detect the follicles and the plurality of parameters associated with each follicle in the 3D ultrasound image.

In an exemplary embodiment, the number of follicles is determined using at least one of the detector 111, the segmenter 112, and the post-processor 113.

In an exemplary embodiment, the post-processor 113 is configured to detect a false follicle detection based on the size of the follicle or the length of the follicle.

In an exemplary embodiment, the follicles is detected by detecting at least one portion of the follicles by the meanshift clustering procedure on the local phase likelihood map, segmenting the follicles by the graph based procedure using the segmenter 112, and post-processing the segmented follicles using the statistical, morphological and distance based procedure by the post-processor 113.

Based on the detected follicles and the plurality of parameters associated with each follicle in the 3D ultrasound image, the tracker 116 is configured to track the detected follicles in the longitudinal scan. In an exemplary embodiment, the detected follicles is tracked by correlating the identity of the detected follicle at the current time with its identity in the longitudinal scans based on the location of the follicle in the ovary with respect to the plurality of anatomical landmarks.

In an exemplary embodiment, the rate of follicular growth is used for predicting dosage schedule for at least one subsequent therapeutic sitting of the subject. In an exemplary embodiment, the size of follicles and ovarian volume in the ovary are computed using the quantifier 113.

Further, the tracker 116 is configured to monitor the rate of growth of each follicle based on the detected parameters in the longitudinal scan. In an exemplary embodiment, the rate of growth of each follicle is monitored by obtaining the parameters associated with each follicle in the longitudinal scans, storing the obtained parameters, and determining the rate of growth of each follicle based on comparison of the stored parameters.

Based on the rate of growth of each follicle, the predictor 117 is configured to determine the dosage of hormone for stimulating the ovary.

In an exemplary embodiment, the predictor 117 is configured to predict the growth of each follicle based on the stored parameters. Further, the quantifier 115 and the predictor 117 are configured to calculate the difference between the predicted growth of each follicle and the determined growth of each follicle periodically. Further, the predictor 117 is configured to dynamically determine the dosage of the hormone based on the calculated difference.

Although FIG. 2B shows the hardware components of the signal processor 110 but it is to be understood that other embodiments are not limited thereon. In other exemplary embodiments, the signal processor 110 may include less or more number of components. Further, the labels or names of the components are used only for illustrative purpose and does not limit the scope of the invention. One or more components can be combined together to perform same or substantially similar function to manage the growth of follicles in the ovary.

FIG. 3 is a flowchart 300 illustrating a method of managing the growth of the follicles in the ovary, according to an exemplary embodiment.

In operation 302, the follicles and the plurality of parameters associated with each follicle are detected in the 3D ultra sound image. In an exemplary embodiment, the method allows the detector 111 to detect the follicles and the plurality of parameters associated with each follicle in the 3D ultra sound image.

In operation 304, the detected follicles in the longitudinal scan are tracked. In an exemplary embodiment, the method allows the tracker 116 to track the detected follicles in the longitudinal scan.

In operation 306, the rate of growth of each follicle is monitored based on the detected parameters in the longitudinal scan. In an exemplary embodiment, the method allows the predictor 117 to monitor the rate of growth of each follicle based on the detected parameters in the longitudinal scan.

In operation 308, the dosage of hormone for stimulating the ovary is determined based on the rate of growth of each follicle. In an exemplary embodiment, the method allows the predictor 117 to determine the dosage of hormone for stimulating the ovary based on the rate of growth of each follicle. The rate of follicular growth is used for predicting the dosage schedule for at least one subsequent therapeutic sitting of the subject.

In operation 310, the report and the nomograph are generated based on the rate of growth of each follicle. In an exemplary embodiment, the method allows the data analyzer 120 to generate the report and the nomograph based on the rate of growth of each follicle.

Unlike the conventional methods, the proposed method can be used to automatically manage the growth of the follicles in the ovary in an accurate manner. The proposed method performs an automatic follicle tracking mechanism and automatic dosage quantification mechanism in an accurate manner.

The proposed method provides an automatic ROI detection function and an ovarian segmentation function. The proposed method allows the longitudinal tracking of the follicles for assisted reproduction in an accurate manner. The proposed method allows the automatic dosage prediction and patient specific models for assisted reproduction. The proposed method provides the follicular quantification in the 3D ultrasound images in an accurate manner.

The proposed method allows longitudinal tracking of the follicles by the follicular quantification in the 3D ultrasound using the global and local feature detectors. The proposed method allows the longitudinal tracking of the follicles by the follicular quantification in the 3D ultrasound images using the spatial locations of the detected follicles.

The proposed method allows the longitudinal tracking of the follicles by the follicular quantification in the 3D ultrasound images using threshold, region and morphology based segmenters. The proposed method allows the longitudinal tracking of the follicles by the follicular quantification in the 3D ultrasound images.

The proposed method allows the longitudinal tracking of the follicles by the follicular quantification in the 3D ultrasound images using the supervised classifiers, the unsupervised classifiers and the state space predictors. The proposed method allows the longitudinal tracking of the follicles by the follicular quantification in the 3D ultrasound images to determine the dosage of hormones for the assisted reproduction in an effective manner.

The operations in the flowchart 300 may be performed in the order presented, in a different order, or simultaneously. Further, in some exemplary embodiments, some of the operations may be omitted, added, modified, skipped, or the like without departing from the scope of the invention.

FIG. 4 is a flowchart of sequential step by step procedures for follicular quantification in the ultrasound image of the ovary, according to an exemplary embodiment. There are three stages in a pipeline to quantify the growth of the follicles. In the first stage, the detector 111 employs mean shift clustering with phase symmetry as the likelihood function. In order to achieve high detection rates, the phase symmetry features are enhanced by a mean suppression procedure. Any of well-known filters such as a Log-Gabor filter, Cauchy filter, etc. that has a non-zero response to a DC input can be employed to determine the phase symmetry feature. A finite number of randomly selected seed points initialize the mean shift procedure. The centers of the follicles are chosen to be the cluster centers obtained after the convergence of the mean shift procedure.

In the second stage of the algorithm, the segmenter 112 employs the detected follicle centers to segment the follicle boundaries. A max-flow algorithm, which belongs to the category of graph based segmentation algorithms, is employed to segment the follicle boundaries. A fixed neighborhood of voxels surrounding the detected follicle centers are connected to a source of the graph and a finite number of voxels that satisfy an intensity constraint on a bounding box of a size larger than the clinically established maximum for follicle size are connected to the sink of the graph. The edge weights are determined as $$w_{ij} = \exp\frac{(I_i - I_j)^2}{\sigma^2}.$$

The results of the segmenter are fed into the third stage of the pipeline which involves the post-processor 113. The role of the post-processor 113 is to split merged follicles based on a gray-weighted distance transform of the segmented follicles and the presence of multiple detections inside the segmentations.

FIG. 5 is a schematic diagram showing an example scenario in which a single follicle is detected based on a mean shift procedure, according to an exemplary embodiment. In an exemplary embodiment, the signal processor 110 is configured to determine the phase symmetry inside the ROI, where the ROI includes an initial point ($X_0$). Further, the signal processor 110 is configured to select a random point (i.e., initial point) in the 3D ultrasound image. Further, the signal processor 110 is configured to apply the mean shift procedure on the random point until convergence. Further, the signal processor 110 is configured to detect the final location of a point ($X_n$) after the convergence, where the final location of the point is the follicle.

FIG. 6 is a schematic diagram showing an example scenario in which multiple follicles are detected based on the mean shift procedure, according to an exemplary embodiment. The signal processor 110 is configured to determine the phase symmetry on the ROI of the image. Further, the signal processor 110 is configured to select a set of random points in the image. After selecting the set of random points in the image, the signal processor 110 is configured to apply the mean shift for all points until convergence. Further, the signal processor 110 is configured to detect the final location points after the convergence, where the final location of the points is the follicles. The random initial points are centered in the follicles after applying the mean shift procedure on a phase symmetry feature map.

FIG. 7 is a flowchart 700 of a method of monitoring a growing condition of the follicles in the ovary, according to an exemplary embodiment.

In operation 702, the input image (e.g., 3D ultra sound image) is obtained. In operation 704, the follicular quantification is performed. In operation 706, the follicular quantification is compared with the previous scan quantification. In operation 708, it is determined whether there is a change in the scan quantification over a period of time. If the scan quantification indicates the change over the period of time, then in operation 710, a healthy growth of follicles is indicated. If the scan quantification does not indicate the change over the period of time, then in operation 712, the method includes indicating irregular follicular growth.

The operations in the flowchart 700 may be performed in the order presented, in a different order, or simultaneously. Further, in some embodiments, some of the operations may be omitted, added, modified, skipped, or the like without departing from the scope of the invention.

FIG. 8 is a diagram showing an example scenario in which growing condition of follicles is determined based on a change in the scan quantification over the period of time, according to an exemplary embodiment. In the scenario, in day 2, the number of follicles is 3; in day 3, the number follicles is 5; in day 4, the number of follicles is 10; and day 5, the number of follicles is 10. Based on this scenario, in day 4 and day 5, the number of follicles is 10, this indicates that the subject has weak follicular growth and requires a medical assistance.

FIG. 9 is a flowchart 900 exemplarily illustrating a method of needle path tracking for the egg retrieval from the dominant follicle, according to an exemplary embodiment.

In operation 902, the input image (i.e., 3D ultrasonic input image) is obtained. In operation 904, the follicular quantification is performed. In operation 906, a probe field of view is determined. In operation 908, the needle field of view displayed in the 3D image is predicted.

The operations in the flowchart 900 may be performed in the order presented, in a different order, or simultaneously. Further, in some embodiments, some of the operations may be omitted, added, modified, skipped, or the like without departing from the scope of the invention.

The needle path tracking for the egg retrieval from the dominant follicle is depicted as shown in FIG. 10. In an exemplary embodiment, the follicle location is determined by the mean shift procedure.

The spatial locations of the follicles are used for surgical planning and needle insertion for the egg retrieval is depicted as shown in FIG. 11.

The number and echogenicity of the follicle and the echogenicity of the ovary are used for computer aided diagnosis (CAD) that is depicted as shown in FIG. 12.

FIG. 13 is a diagram of a system 1300 for processing the ultrasound image, according to an exemplary embodiment. The system 1300 includes a front end 1310, a mid end 1320 and a back end 1330. The back end 1330 includes the ultrasound imaging apparatus 100. The operations and functions of the ultrasound imaging apparatus 100 are explained in conjunction with FIGS. 1 and 2A. The front end 1310, the mid end 1320 and the back end 1330 communicate with each other through a communication unit (not shown). The back end 1330 receives the ultrasound data from the front end 1310.

FIG. 14 is a schematic diagram of a system 1400 for acquiring and processing the ultrasound image, according to an exemplary embodiment. The system 1400 includes a pulser 1410, a transducer 1420, an analog front end 1430, the ultrasound processing system 1300 and a display unit 1440. The operations and functions of the ultrasound processing system 1300 is explained in FIG. 13. The pulser 1410 sends out an electric pulse/pulse train to the transducer 1420. The transducer 1420 converts this electric pulse into an ultrasound wave and transmits the ultrasound wave to the object of interest. The back scattered ultrasound waves are received at the analog front end 1430 through the beamformer (not shown). The envelope of the radio frequency data is recovered by the ultrasound processing system 1300 and log compressed to form a B-mode ultrasound image which is displayed by the display unit 1440.

FIG. 15 is a schematic diagram including a nomograph illustrating the rate of growth of each follicle, according to an exemplary embodiment. The nomograph illustrates the growth rate of the follicles over time (i.e., days VS follicle diameter). Further, the nomograph indicates the dosage administered over time, so as to predict the ovarian response.

The exemplary embodiments disclosed herein can be implemented using at least one software program running on at least one hardware device and performing network management functions to control the elements.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those of ordinary skill in the art will recognize that the embodiments herein can be practiced with modification within the spirit and scope of the embodiments as described herein.

The invention claimed is:

1. A method of managing growth of follicles in an ovary, the method comprising:
    detecting, by a signal processor, the follicles and a plurality of parameters associated with each follicle among the follicles, in a three dimensional (3D) ultra sound image obtained at a plurality of time intervals;
    tracking the detected follicles, in a longitudinal scan;
    monitoring a rate of growth of each follicle based on the detected plurality of parameters, in the longitudinal scan, wherein the monitoring of the rate of growth of each follicle based on the detected plurality of parameters comprises:
        obtaining the plurality of parameters associated with each follicle in the longitudinal scan at each of the plurality of time intervals;
        storing the obtained plurality of parameters; and
        determining the rate of growth of each follicle based on a comparison of the stored plurality of parameters obtained at the each of the plurality of time intervals;
    predicting a growth of the each follicle based on the stored plurality of parameters;
    calculating a difference between the predicted growth of each follicle and a growth of each follicle;
    determining a dosage of a hormone for stimulating the ovary, based on the rate of growth of each follicle and the calculated difference between the predicted growth of each follicle and the growth of each follicle; and
    generating a report and a nomograph, based on the rate of growth of each follicle.

2. The method of claim 1, wherein the plurality of parameters comprise at least one of the number of the follicles in the ovary, a size of the each follicle among the follicles in the ovary, a volume of the each follicle, a diameter of the each follicle, an average length of the follicles, an identity of the each follicle, and a location of the each follicle in the ovary with respect to a plurality of anatomical landmarks.

3. The method of claim 2, wherein the plurality of anatomical landmarks comprise at least one of ovarian vessels, an endometrium, a boundary of a uterus, fallopian tubes, a medulla of the ovary, a soft tissue in the ovary, a junctional zone, a corpus luteum, imaging artifacts, and anatomical structures that are visible in the ultrasound image.

4. The method of claim 1, wherein the detecting of the follicles comprises:
   detecting at least one portion of the follicles by using a mean-shift clustering procedure;
   segmenting the follicles by using a graph based procedure; and
   post-processing the segmented follicles by using statistical, morphological, and distance based methods.

5. The method of claim 1, wherein the longitudinal scan comprises images obtained at different time intervals.

6. The method of claim 1, wherein the tracking of the detected follicles comprises correlating an identity of a detected follicle at a current time with its identity in the longitudinal scans based on a location of the follicle in the ovary with respect to a plurality of anatomical landmarks.

7. The method of claim 1, wherein the generating of the report and the nomograph comprises:
   plotting the rate of growth of each follicle over time;
   plotting the dosage administered over time;
   predicting an ovarian response;
   categorizing a subject into a poor responder and a good responder, based on the ovarian response; and
   generating a document consolidating the plurality of parameters with regard to detecting, tracking and monitoring the growth of each follicle along with the dosage.

8. The method of claim 1, wherein the plurality of parameters associated with the each follicle are continuously monitored for diagnosing disorders in the ovary.

9. An apparatus for managing growth of follicles in an ovary, the apparatus comprising:
   a storage; and
   a signal processor coupled with the storage, wherein the signal processor is configured to:
      detect the follicles and a plurality of parameters associated with each follicle among the follicles, in a three dimensional (3D) ultra sound image obtained at a plurality of time intervals;
      track the detected follicles, in a longitudinal scan;
      monitor a rate of growth of each follicle based on the detected plurality of parameters, in the longitudinal scan, wherein the monitoring of the rate of growth of each follicle based on the detected plurality of parameters comprises:
         obtaining the plurality of parameters associated with each follicle in the longitudinal scan at each of the plurality of time intervals;
         storing the obtained plurality of parameters; and
         determining the rate of growth of each follicle based on a comparison of the stored plurality of parameters;
      predict a growth of the each follicle based on the plurality of stored parameters obtained at the each of the plurality of time intervals;
      calculate a difference between the predicted growth of each follicle and a growth of each follicle;
      determine a dosage of a hormone for stimulating the ovary based on the rate of growth of each follicle and the calculated difference between the predicted growth of each follicle and the growth of each follicle; and
      generate a report and a nomograph based on the rate of growth of the each follicle.

10. The apparatus of claim 9, wherein the plurality of parameters comprises at least one of the number of the follicles in the ovary, a size of a follicle in the ovary, a volume of the follicle, a diameter of the follicle, an average length of the follicle, an identity of the follicle, and a location of the follicle in the ovary with respect to a plurality of anatomical landmarks.

11. The apparatus of claim 10, wherein the plurality of anatomical landmarks comprise of at least one of ovarian vessels, an endometrium, a boundary of a uterus, fallopian tubes, a medulla of the ovary, a soft tissue in the ovary, a junctional zone, a corpus luteum, imaging artifacts, and anatomical structures that are visible in the ultrasound image.

12. The apparatus of claim 9, wherein, in the detecting of the follicles, the signal processor is further configured to:
   detect at least one portion of the follicles by using a mean-shift clustering procedure;
   segment the follicles by using a graph based procedure; and
   post-process the segmented follicles by using statistical, morphological, and distance based methods.

13. A non-transitory computer readable medium having embodied thereon a program for executing a method, the method comprising:
   detecting, by a signal processor, the follicles and a plurality of parameters associated with each follicle among the follicles, in a three dimensional (3D) ultra sound image obtained at a plurality of time intervals;
   tracking the detected follicles, in a longitudinal scan;
   monitoring a rate of growth of each follicle based on the detected plurality of parameters, in the longitudinal scan, wherein the monitoring of the rate of growth of each follicle based on the detected plurality of parameters comprises:
      obtaining the plurality of parameters associated with each follicle in the longitudinal scan at each of the plurality of time intervals;
      storing the plurality of obtained parameters; and
      determining the rate of growth of each follicle based on a comparison of the stored plurality of parameters obtained at the each of the plurality of time intervals;
   predicting a growth of the each follicle based on the stored plurality of parameters;
   calculating a difference between the predicted growth of each follicle and a growth of each follicle; and
   determining a dosage of a hormone for stimulating the ovary, based on the rate of growth of each follicle and the calculated difference between the predicted growth of each follicle and the growth of each follicle; and
   generating a report and a nomograph, based on the rate of growth of each follicle.

* * * * *